United States Patent
Nabel et al.

(10) Patent No.: US 6,297,219 B1
(45) Date of Patent: Oct. 2, 2001

(54) SITE-SPECIFIC INSTILLATION OF CELLS OR SITE-SPECIFIC TRANSFORMATION OF CELLS AND KITS THEREFOR

(75) Inventors: Elizabeth G. Nabel; Gary J. Nabel, both of Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 08/889,399

(22) Filed: Jul. 8, 1997

Related U.S. Application Data

(63) Continuation of application No. 08/376,522, filed on Jan. 23, 1995, now Pat. No. 5,698,531, which is a continuation of application No. 07/724,509, filed on Jun. 28, 1991, now abandoned, which is a continuation-in-part of application No. 07/331,366, filed on Mar. 31, 1989, now abandoned.

(51) Int. Cl.[7] ............... A61K 48/00; C12N 15/63
(52) U.S. Cl. ............ 514/44; 424/93.21; 435/320.1; 435/375
(58) Field of Search ............ 514/44; 424/93.21; 435/375

(56) References Cited

U.S. PATENT DOCUMENTS

| | | | |
|---|---|---|---|
| 4,332,893 | 6/1982 | Rosenberg | 435/70.3 |
| 4,353,888 | 10/1982 | Sefton | 424/424 |
| 4,636,195 | 1/1987 | Wolinsky | 604/509 |
| 4,824,436 | 4/1989 | Wolinsky | 604/509 |
| 4,874,746 | 10/1989 | Antoniades et al. | 514/21 |
| 5,087,617 | 2/1992 | Smith | 514/44 |
| 5,580,859 | 12/1996 | Felgner et al. | 514/44 |
| 5,589,466 | 12/1996 | Felgner et al. | 514/44 |
| 5,662,896 | * 9/1997 | Barber et al. | 424/93.21 |
| 5,707,969 | 1/1998 | Nabel et al. | 514/44 |
| 5,997,859 | * 12/1999 | Barber et al. | 424/93.2 |

FOREIGN PATENT DOCUMENTS

| | | |
|---|---|---|
| 0 273 085 | 7/1988 | (EP) . |
| WO 90/11092 | 10/1990 | (WO) . |
| WO 90/11734 | 10/1990 | (WO) . |

OTHER PUBLICATIONS

Arai, et al., "Gene Transfer of Fas Ligand Induces Tumor Regression In Vivo", *Proc. Natl. Acad. Sci. USA* (Dec. 1997), vol. 94, pp. 13862–13867.
Arai, et al., "Inhibition of the Alloantibody Response by CD95 Ligad", *Nat. Med.* (Aug. 1997), vol. 3(8), pp. 843–848.
Broadley et al., *Federation of American Societies for Experimental Biology Journal,* vol. 5, No. 4, pp. 539A, abstract 977, "Transfection of wounds in vivo with Transforming Growth Factor–B Accelerates Healing", 1991.
Brown, D., "Gene Therapy 'Oversold' by Researhers, Journalists", *The Washington Post* (Dec. 8, 1995), A22.
Bubenik, et al., "Local Administration of Cells Containing an Inserted IL–2 Gene and Producing IL–2 Inhibits Growth of Human Tumours in nu/nu Mice", *Immunol. Letters* (1988), 19(4), pp. 279–282.
Coghlan, A., "Gene Dream Fades Away", *New Scientist* (1995), vol. 145, pp. 14–15.
Felgner, et al., "Lipofection: A Highly Efficient, Lipid–Mediated DNA—Transfection Procedure", *Proc. Natl. Acad. Sci. USA* (Nov. 1987), vol.84, pp. 7413–7417.
Mulligan, R.C., "The Basic Science of Gene Therapy", *Science* (1993), vol. 260, pp. 926–930.
Nabel, "Recombinant Gene Expression in vivo Within Endothelial Cells of the Arterial Wall", *Science* (Jun. 1989), vol. 244, pp. 1342–1344.
Nabel, et al., "Clinical Protocol: Immunotherapy for Cancer by Direct Gene Transfer into Tumors", *Human Gene Therapy* (1994), vol. 5, pp. 57–77.
Nabel, et al., "Site–Specific Gene Expression In Vivo by Direct Gene Transfer into the Arterial Wall", *Science* (Sep. 14, 1990), vol. 249, pp. 1285–1288.
Nabel, et al., "Immune Response in Human Melanoma After Transfer of an Allogeneic Class I Major Histocompatibility Complex Gene with DNA—Liposome Complexes", *Proc. Natl. Acad. sci. USA* (Dec. 1996), vol. 93, pp. 15388–15393.
Nabel, et al., "Direct Gene Transfer with DNA—Liposome Complexes in Melanoma: Expression, Biologic Activity, and Lack of Toxicity in Humans", *Proc. Natl. Acad. Sci. USA* (Dec. 1993), vol. 90, pp. 11307–11311.
Nabel G.J., "Clinical Protocol: Response to the Points to Consider for Immunotherapy of Malignancy by In Vivo Gene Transfer into Tumors", *Human Gene Therapy* (1992), vol. 3, pp. 705–711.
Ogura, et al., "Implantation of Genetically Manipulated Fibroblasts into Mice as Antitumor Alpha–Interferon Therapy", *Cancer Research* (Aug. 15, 1990), vol. 50, pp. 5102–5106.
Plautz, et al., "Immunotherapy of Malignancy by In Vivo Gene Transfer into Tumors", *Proc. Natl. Acad. Sci. USA* (May 1993), vol. 90, pp. 4645–4649.

(List continued on next page.)

*Primary Examiner*—Karen M. Hauda
*Assistant Examiner*—Anne Marie S. Beckerleg
(74) *Attorney, Agent, or Firm*—Brink Hofer Gilson & Lione

(57) ABSTRACT

A method for the direct in vivo transformation of cells in and surrounding a solid tumor is disclosed. This method is based on the site-specific delivery of proteins to solid tumors and to tissue surrounding the solid tumor by direct injection of a nucleic acid sequence. In particular, this method is directed to site-specific delivery of nucleic acids encoding major histocompatibility proteins, cytokines, and toxins to a solid tumor. This technique provides for the transfer of vectors and expression of recombinant genes in vivo and allows the introduction of proteins of therapeutic or diagnostic value for the treatment of disease.

24 Claims, 2 Drawing Sheets

OTHER PUBLICATIONS

Selden, "Implantation of Genetically Engineered Fibroblasts into Mice: Implications for Gene Therapy", *Science* (May 1987), vol. 236, pp. 714–718.

Tanaka, et al., "Reversal of Oncogenesis by the Expression of a Major Histocompatibility Complex Class I Gene", *Science* (Apr. 5, 985), vol. 228, pp. 26–30.

Wang, et al., "Highly Efficient DNA Delivery Mediated by pH–Sensitive Immunoliposomes", *Biochemistry* (1989), vol. 28, pp. 9508–9514.

Wilson, et al., "Implantation of Vascular Grafts Lined with Genetically Modified Endothelial Cells", *Science* (Jun. 16, 1989), vol. 244, pp. 1344–1346.

Wolff, et al., "Direct Gene Transfer into Mouse Muscle In Vivo", *Science* (Mar. 23, 1990), vol. 247, pp. 1465–1468.

Zwiebel, "High–Level Recombinant Gene Expression in Rabbit Endothelial Cells Transduced by Retroviral Vectors", *Science* (Jan. 1989), vol. 243, pp. 220–222.

J. Zwiebel et al., "High–Level Recombinant Gene Expression in Rabbit Endothelial Cells Transduced by Retroviral Vectors", *Science,* vol. 243, pp. 220–222 (1989).

E. Nabel et al., "Recombinant Gene Expression in Vivo Within Endothelial Cells of the Arterial Wall", *Science,* vol. 244, pp. 1342–1344 (1989).

J. Wilson et al., "Implantation of Vascular Grafts Lined with Genetically Modified Endothelial Cells", *Science,* vol. 244, pp. 1344–1346 (1989).

R. Selden et al, "Implantation of Genetically Engineered Fibroblasts into Mice: Implications for Gene Therapy", *Science,* vol. 236 pp. 714–718, (1987).

H. Ogura et al., "Implantation of Genetically Manipulated Fibroblasts into Mice as Antitumor α—Interferon Therapy", *Cancer Research,* vol. 50, pp. 5102–5106 (1990).

K. Broadley et al., "Transfection of Wounds in Vivo with Transforming Growth Factor–$\beta_1$ Accelerates Healing", *The FASEB Journal,* vol. 5, No. 11 p. a539 (1991).

P. Felgner et al., "Lipofection: A Highly efficient, lipid–mediated DNA–transfection procedure", *Proc. Natl. Acad. Sci. USA,* vol. 84, No. 21, pp. 7413–7417 (1987).

\* cited by examiner

SITE-SPECIFIC INSTILLATION OF CELLS OR SITE-SPECIFIC TRANSFORMATION OF CELLS AND KITS THEREFOR

This application is a continuation of application No. 08/376,522, filed Jan. 23, 1995 issued as U.S. Pat. No. 5,698,531 on Jan 16, 1997, which is a continuation of application No. 07/724,509, filed Jun. 28, 1991 Abn, which is a continuation in part of application No. 07/331,366, filed Mar. 31, 1989 now abandoned.

BACKGROUND OF THE INVENTION

1. Field of the Invention

The present invention relates to the treatment of diseases by the site-specific instillation or transformation of cells and kits therefor.

2. Discussion of the Background

The effective treatment of many systemic and inherited diseases remains a major challenge to modern medicine. The ability to deliver therapeutic agents to specific sites in vivo would be an asset in the treatment of, e.g., localized diseases. In addition the ability to cause a therapeutic agent to perfuse through the circulatory system would be effective for the treatment of, e.g., systemic diseases.

For example, it would be desirable to administer in a steady fashion an antitumor agent or toxin in close proximity to a tumor. Similarly, it would be desirable to cause a perfusion of, e.g., insulin in the blood of a person suffering from diabetes. However, for many therapeutic agents there is no satisfactory method of either site-specific or systemic administration.

In addition, for many diseases, it would be desirable to cause, either locally or systemically, the expression of a defective endogenous gene, the expression of a exogenous gene, or the suppression of an endogenous gene. Again, these remain unrealized goals.

In particular, the pathogenesis of atherosclerosis is characterized by three fundamental biological processes. These are: 1) proliferation of intimal smooth muscle cells together with accumulated macrophages; 2) formation by the proliferated smooth muscle cells of large amounts of connective tissue matrix; and 3) accumulation of lipid, principally in the form of cholesterol esters and free cholesterol, within cells as well as in surrounding-connective tissue.

Endothelial cell injury is an initiating event and is manifested by interference with the permeability barrier of the endothelium, alterations in the non-thrombogenic properties of the endothelial surface, and promotion of procoagulant properties of the endothelium. Monocytes migrate between endothelial cells, become active as scavenger cells, and differentiate into macrophages.

Macrophages then synthesize and secrete growth factors including platelet derived growth factor (PDGF), fibroblast growth factor (FGF), epidermal growth factor (EGF), and transforming growth factor alpha TGF-α). These growth factors are extremely potent in stimulating the migration and proliferation of fibroblasts and smooth muscle cells in the atherosclerotic plaque. In addition, platelets may interact with the injured endothelial cell and the activated macrophage to potentiate the elaboration of growth factors and thrombus formation.

Two major problems in the clinical management of coronary artery disease include thrombus formation in acute myocardial ischemia and restenosis following coronary angioplasty (PTCA). Both involve common cellular events, including endothelial injury and release of potent growth factors by activated macrophages and platelets. Coronary angioplasty produces fracturing of the atherosclerotic plaque and removal of the endothelium. This vascular trauma promotes platelet aggregation and thrombus formation at the PTCA site. Further release of mitogens from platelets and macrophages, smooth muscle cell proliferation and monocyte infiltration result in restenosis.

Empiric therapy with antiplatelet drugs has not prevented this problem, which occurs in one-third of patients undergoing PTCA. A solution to restenosis is to prevent platelet aggregation, thrombus formation, and smooth muscle cell proliferation.

Thrombus formation is also a critical cellular event in the transition from stable to unstable coronary syndromes. The pathogenesis most likely involves acute endothelial cell injury and or plaque rupture, promoting dysjunction of endothelial cell attachment, and leading to the exposure of underlying macrophage foam cells. This permits the opportunity for circulating platelets to adhere, aggregate, and form thrombi.

The intravenous administration of thrombolytic agents, such as tissue plasminogen activator (tPA) results in lysis of thrombus in approximately 70% of patients experiencing an acute myocardial infarction. Nonetheless, approximately 30% of patients fail to reperfuse, and of those patients who undergo initial reperfusion of the infarct related artery, approximately 25% experience recurrent thrombosis within 24 hours. Therefore, an effective therapy for rethrombosis remains a major therapeutic challenge facing the medical community today.

As noted above, an effective therapy for rethrombosis is by far not the only major therapeutic challenge existing today. Others include the treatment of other ischemic conditions, including unstable angina, myocardial infarction or chronic tissue ischemia, or even the treatment of systemic and inherited diseases or cancers. These might be treated by the effective administration of anticoagulants, vasodilatory, angiogenic, growth factors or growth inhibitors to a patient. Thus, there remains a strongly felt need for an effective therapy in all of these clinical settings.

SUMMARY OF THE INVENTION

Accordingly, one object of the present invention is to provide a novel method for the site-specific administration of a therapeutic agent.

It is another object of the present invention to provide a method for the perfusion of a therapeutic agent in the blood stream of a patient.

It is another object of the present invention to provide a method for causing the expression of an exogenous gene in a patient.

It is another object of the present invention to provide a method for causing the expression of a defective endogenous gene in a patient.

It is another object of the present invention to provide a method for suppressing the expression of an endogenous gene in a patient.

It is another object of the present invention to provide a method for site-specifically replacing damaged cells in a patient.

It is another object of the present invention to provide a method for the treatment of a disease by causing either the site-specific administration of a therapeutic agent or the perfusion of a therapeutic agent in the bloodstream of a patient.

It is another object of the present invention to provide a method for the treatment of a disease by causing either the expression of an exogenous gene, the expression of a defective endogenous gene, or the suppression of the expression of an endogenous gene in a patient.

It is another object of the present invention to provide a method for the treatment of a disease by site-specifically replacing damaged cells in a patient.

It is another object of the present invention to provide a kit for site-specifically instilling normal or transformed cells in a patient.

It is another object of the present invention to provide a kit for site-specifically transforming cells in vivo.

These and other objects of this invention which will become apparent during the course of the following detailed description of the invention have been discovered by the inventors to be achieved by (a) a method which comprises either (i) site-specific instillation or either normal (untransformed) or transformed cells in a patient or (ii) site-specific transformation of cells in a patient and (b) a kit which contains a catheter for (i) site-specific instillation of either normal or transformed cells or (ii) site-specific transformation of cells.

Site-specific instillation of normal cells can be used to replace damaged cells, while instillation of transformed cells can be used to cause the expression of either a defective endogenous gene or an exogenous gene or the suppression of an endogenous gene product. Instillation of cells in the walls of the patient's blood vessels can be used to cause the steady perfusion of a therapeutic agent in the blood stream.

BRIEF DESCRIPTION OF THE DRAWINGS

A more complete appreciation of the invention and many of the attendant advantages thereof will be readily obtained as the same become better understood by reference to the following detailed description when considered in connection with the accompanying figures, wherein.

DETAILED DESCRIPTION OF THE PREFERRED EMBODIMENTS

Thus, in one embodiment, the present invention is used to treat diseases, such as inherited diseases, systemic diseases, diseases of the cardiovascular system, diseases of particular organs, or tumors by instilling normal or transformed cells or by transforming cells.

The cells which may be instilled in the present method include endothelium, smooth muscle, fibroblasts, monocytes, macrophages, and parenchymal cells. These cells may produce proteins which may have a therapeutic or diagnostic effect and which may be naturally occurring or arise from recombinant genetic material.

Figure 1:
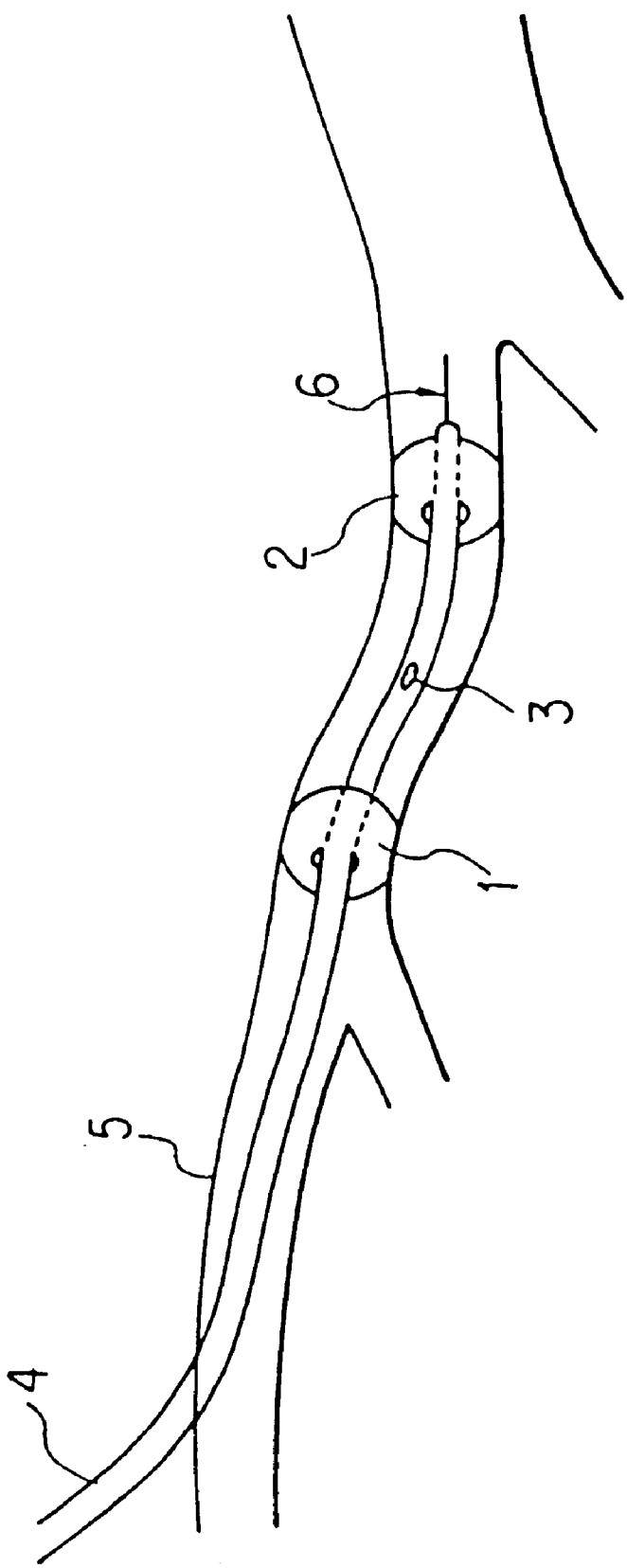
FIGS. 1 and 2 illustrate the use of a catheter in accordance with the invention to surgically or percutaneously implant cells in a blood vessel or to transform in vivo cells present on the wall of a patient's blood vessel.
Figure 2:
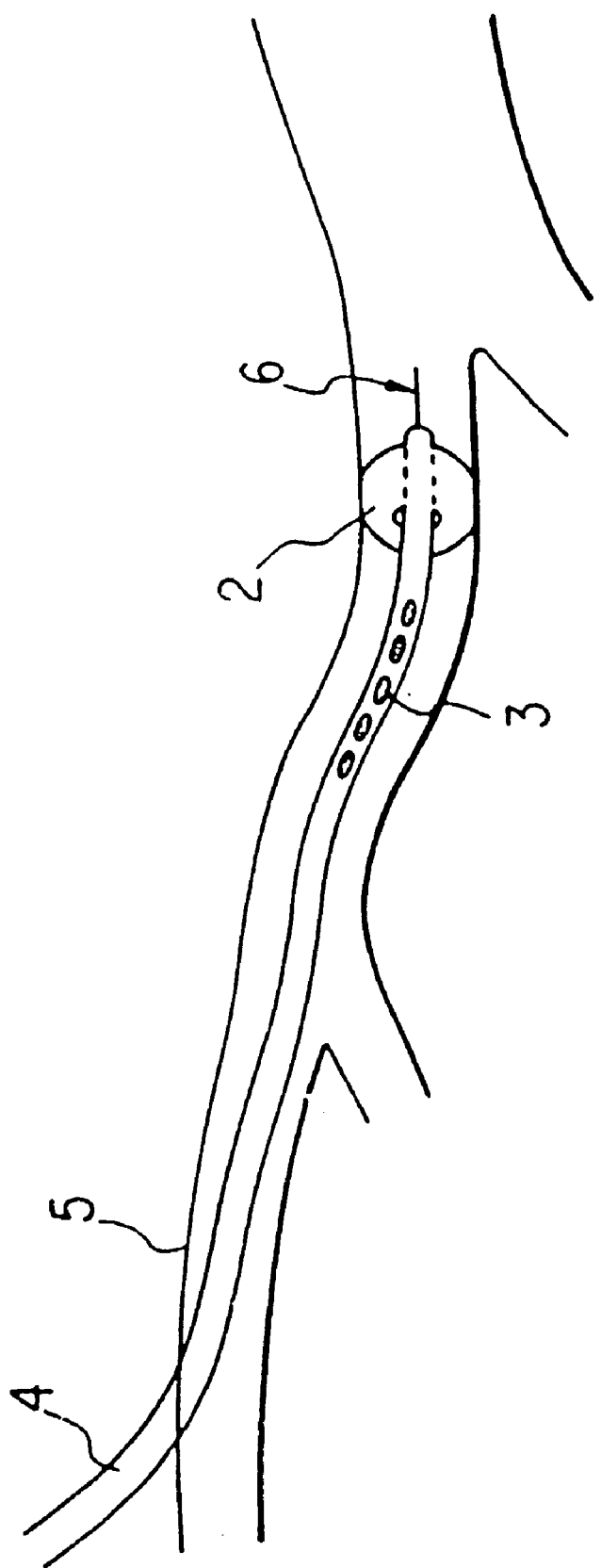

Referring now to the figures, wherein like reference numerals designate identical or corresponding parts throughout the several views, and more particularly to FIG. 1 thereof, this figure illustrates the practice of the present invention with a catheter having a design as disclosed in U.S. Pat. No. 4,636,195, which is hereby incorporated by reference. This catheter may be used to provide normal or genetically altered cells on the walls of a vessel or to introduce vectors for the local transformation of cells. In the figure, 5 is the wall of the blood vessel, The figure shows the catheter body 4 held in place by the inflation of inflatable balloon means 1 and 2. The section of the catheter body 4 situated between balloon means 1 and 2 is equipped with instillation port means 3. The catheter may be further equipped with a guidewire means 6. FIG. 2 illustrates the use of a similar catheter, distinguished from the catheter illustrated in FIG. 1 by the fact that it is equipped with only a single inflatable balloon means 2 and a plurality of instillation port means 3. This catheter may contain up to twelve individual instillation port means 3, with five being illustrated.

In the case of delivery to an organ, the catheter may be introduced into the major artery supplying the tissue. Cells containing recombinant genes or vectors can be introduced through a central instillation port after temporary occlusion of the arterial circulation. In this way, cells or vector DNA may be delivered to a large amount of parenchymal tissue distributed through the capillary circulation. Recombinant genes can also be introduced into the vasculature using the double balloon catheter technique in the arterial circulation proximal to the target organ. In this way, the recombinant genes may be secreted directly into the circulation which perfuse the involved tissue or may be synthesized directly within the organ.

In one embodiment, the therapeutic agents are secreted by vascular cells supplying specific organs affected by the disease. For example, ischemic cardiomyopathy may be treated by introducing angiogenic factors into the coronary circulation. This approach may also be used for peripheral vascular or cerebrovascular diseases where angiogenic factors may improve circulation to the brain or other tissues. Diabetes mellitus may be treated by introduction of glucose-responsive insulin secreting cells in the portal circulation where the liver normally sees a higher insulin concentration than other tissues.

In addition to providing local concentrations of therapeutic agents, the present method may also be used for delivery of recombinant genes to parenchymal tissues, because high concentrations of viral vector and other vectors can be delivered to a specific circulation. Using this approach, deficiencies of organ-specific proteins may also be treated. For example, in the liver, $\alpha$-antitrypsin inhibitor deficiency or hyperchloresterolemia may be treated by introduction of a-antitrypsin or the LDL receptor gene. In addition, this approach may be used for the treatment of a malignancy. Secretion of specific recombinant toxin genes into the circulation of inoperable tumors provides a therapeutic effect. Examples include acoustic neuromas or certain hemangiomas which are otherwise unresurrectable.

In clinical settings, these therapeutic recombinant genes are introduced in cells supplying the circulation of the involved organ. Although the arterial and capillary circulations are the preferred locations for introduction of these cells, venous systems are also suitable.

In its application to the treatment of local vascular damage the present invention provides for the expression of proteins which ameliorate this condition in situ. In one embodiment, because vascular cells are found at these sites, they are used as carriers to convey the therapeutic agents.

The invention thus, in one of its aspects, relies on genetic alteration of endothelial and other vascular cells or somatic cell gene therapy, for transmitting therapeutic agents (i.e., proteins, growth factors) to the localized region of vessel injury. To successfully use gene transplantation in the cells, four requirements must be fulfilled. First, the gene which is to be implanted into the cell must be identified and isolated.

Second, the gene to be expressed must be cloned and available for genetic manipulation. Third, the gene must be introduced into the cell in a form that will be expressed or functional. Fourth, the genetically altered cells must be situated in the vascular region where it is needed.

In accordance with the present invention the altered cells or appropriate vector may be surgically, percutaneously, or intravenously introduced and attached to a section of a patient's vessel wall. Alternatively, some of the cells existing on the patient's vessel wall are transformed with the desired genetic material or by directly applying the vector. In some instances, vascular cells which are not genetically modified can be introduced by these methods to replace cells lost or damaged on the vessel surface.

Any blood vessel may be treated in accordance with this invention; that is, arteries, veins, and capillaries. These blood vessels may be in or near any organ in the human, or mammalian, body.

Introduction of normal or genetically altered cells into a blood vessel:

This embodiment of the invention may be illustrated as follows:

I. Establishment of endothelial or other vascular cells in tissue culture.

Initially, a cell line is established and stored in liquid nitrogen. Prior to cryopreservation, an aliquot is taken for infection or transfection with a vector, viral or otherwise, containing the desired genetic material.

Endothelial or other vascular cells may be derived enzymatically from a segment of a blood vessel, using techniques previously described in J. W. Ford, et al., *In Vitro*, 17, 40 (1981). The vessel is excised, inverted over a stainless steel rod and incubated in 0.1% trypsin in $Ca^{++}$- and $Mg^{++}$- free Hank's balanced salt solution (BSS) with 0.125% EDTA at pH 8 for 10 min at 37° C.

Cells (0.4 to $1.5 \times 10^6$) are collected by centrifugation and resuspended in medium 199 (GIBCO) containing 10% fetal bovine serum, endothelial cell growth supplement (ECGS, Collaborative Research, Waltham, Mass.) at 25 $\mu$g/ml, heparin at 15 U/ml, and gentamicin (50 $\mu$g/ml). Cells are added to a 75 $cm^2$ tissue culture flask precoated with gelatin (2 mg/ml in distilled water). Cells are fed every second day in the above medium until they reach confluence.

After two weeks in culture, the ECGS and heparin may be omitted from the medium when culturing porcine endothelium. If vascular smooth muscle cells or fibroblasts are desired the heparin and ECGS can be omitted entirely from the culturing procedure. Aliquots of cells are stored in liquid nitrogen by resuspending to approximately $10^6$ cells in 0.5 ml of ice cold fetal calf serum on ice. An equal volume of ice cold fetal calf serum containing 10% DMSO is added, and cells are transferred to a prechilled screw cap Corning freezing tube. These cells are transferred to a −70° C. freezer for 3 hours before long term storage in liquid nitrogen.

The cells are then infected with a vector containing the desired genetic material.

II. Introduction of cells expressing normal or exogenous proteins into the vasculature.

A. Introduction of cells expressing relevant proteins by catheterization.

The patient is prepared for catheterization either by surgery or percutaneously, observing strict adherence to sterile techniques. A cutdown procedure is performed over the target blood vessel or a needle is inserted into the target blood vessel after appropriate anesthesia. The vessel (5) is punctured and a catheter, such as described in U.S. Pat. No. 4,636,195, which is hereby incorporated by reference (available from USCI, Billerica, Mass.) is advanced by guidewire means (6) under fluoroscopic guidance, if necessary, into the vessel (5) (FIG. 1). This catheter means (4) is designed to introduce infected endothelial cells into a discrete region of the artery. The catheter has a proximal and distal balloon means (2) and (1), respectively, (e.g., each balloon means may be about 3 mm in length and about 4 mm in width), with a length of catheter means between the balloons. The length of catheter means between the balloons has a port means connected to an instillation port means (3). When the proximal and distal balloons are inflated, a central space is created in the vessel, allowing for instillation of infected cells though the port.

A region of the blood vessel is identified by anatomical landmarks and the proximal balloon means (2) is inflated to denude the endothelium by mechanical trauma (e.g., by forceful passage of a partially inflated balloon catheter within the vessel) or by mechanical trauma in combination with small amounts of a proteolytic enzyme such as dispase, trypsin, collagenase, papain, pepsin, chymotrypsin or cathepsin, or by incubation with these proteolytic enzymes alone. In addition to proteolytic enzymes, lipases may be used. The region of the blood vessel may also be denuded by treatment with a mild detergent or the like, such as NP-40, Triton X100, deoxycholate, or SDS.

The denudation conditions are adjusted to achieve essentially complete loss of endothelium for cell transfers or approximately 20 to 90%, preferably 50 to 75%, loss of cells from the vessel wall for direct infection. In some instances cell removal may not be necessary. The catheter is then advanced so that the instillation port means (3) is placed in the region of denuded endothelium. Infected, transfected or normal cells are then instilled into the discrete section of artery over thirty minutes. If the blood vessel is perfusing an organ which can tolerate some ischemia, e.g., skeletal muscle, distal perfusion is not a major problem, but can be restored by an external shunt if necessary, or by using a catheter which allows distal perfusion. After instillation of the infected endothelial cells, the balloon catheter is removed, and the arterial puncture site and local skin incision are repaired. If distal perfusion is necessary, an alternative catheter designed to allow distal perfusion may be used.

B. Introduction of recombinant genes directly into cells on the wall of a blood vessel or perfused by a specific circulation in vivo; infection or transfection of cells on the vessel wall and organs.

Surgical techniques are used as described above. Instead of using infected cells, a high titer desired genetic material transducing viral vector ($10^5$ to $10^6$ particles/ml) or DNA complexed to a delivery vector is directly instilled into the vessel wall using the double balloon catheter technique. This vector is instilled in medium containing serum and polybrene (10 $\mu$g/ml) to enhance the efficiency of infection. After incubation in the dead space created by the catheter for an adequate period of time (0.2 to 2 hours or greater), this medium is evacuated, gently washed with phosphate-buffered saline, and arterial circulation is restored. Similar protocols are used for post operative recovery.

The vessel surface can be prepared by mechanical denudation alone, in combination with small amounts of proteolytic enzymes such as dispase, trypsin, collagenase or cathepsin, or by incubation with these proteolytic enzymes alone. The denudation conditions are adjusted to achieve the appropriate loss of cells from the vessel wall.

Viral vector or DNA-vector complex is instilled in Dulbecco's modified Eagle's medium using purified virus or complexes containing autologous serum, and adhesive molecules such as polybrene (10 μg/ml), poly-L-lysine, dextran sulfate, or any polycationic substance which is physiologically suitable, or a hybrid antibody directed against the envelope glycoprotein of the virus or the vector and the relevant target in the vessel wall or in the tissue perfused by the vessel to enhance the efficiency of infection by increasing adhesion of viral particles to the relevant target cells. The hybrid antibody directed against the envelope glycoprotein of the virus or the vector and the relevant target cell can be made by one of two methods. Antibodies directed against different epitopes can be chemically crosslinked (G. Jung, C. J. Honsik, R. A. Reisfeld, and H. J. Muller-Eberhard, *Proc. Natl. Acad. Sci. USA,* 83, 4479 (1986); U. D. Staerz, O. Kanagawa, and M. J. Bevan, *Nature,* 314, 628 (1985); and P. Perez, R. W. Hoffman, J. A. Titus, and D. M. Segal, *J. Exp. Med.,* 163, 166 (1986)) or biologically coupled using hybrid hybridomas (U. D. Staerz and M. J. Bevan, *Proc. Natl. Acad. Sci. USA,* 83, 1453 (1986); and C. Milstein and A. C. Cuello, *Nature,* 305, 537 (1983)). After incubation in the central space of the catheter for 0.2 to 2 hours or more, the medium is evacuated, gently washed with phosphate buffered saline, and circulation restored.

Using a different catheter design (See FIG. 2), a different protocol for instillation can also be used. This second approach involves the use of a single balloon means (2) catheter with multiple port means (3) which allow for high pressure delivery of the retrovirus into partially denuded arterial segments. The vessel surface is prepared as described above and defective vector is introduced using similar adhesive molecules. In this instance, the use of a high pressure delivery system serves to optimize the interaction of vectors with cells in adjacent vascular tissue.

The present invention also provides for the use of growth factors delivered locally by catheter or systemically to enhance the efficiency of infection. In addition to retroviral vectors, herpes virus, adenovirus, or other viral vectors are suitable vectors for the present technique.

It is also possible to transform cells within an organ or tissue. Direct transformation of organ or tissue cells may be accomplished by one of two methods. In a first method a high pressure transfection is used. The high pressure will cause the vector to migrate through the blood vessel walls into the surrounding tissue. In a second method, injection into a capillary bed, optionally after injury to allow leaking, gives rise to direct infection of the surrounding tissues.

The time required for the instillation of the vectors or cells will depend on the particular aspect of the invention being employed. Thus, for instilling cells or vectors in a blood vessel a suitable time would be from 0.01 to 12 hrs, preferably 0.1 to 6 hrs, most preferably 0.2 to 2 hrs. Alternatively for high pressure instillation of vectors or cells, shorter times might be preferred.

Obtaining the cells used in this invention:

The term "genetic material" generally refers to DNA which codes for a protein. This term also encompasses RNA when used with an RNA virus or other vector based on RNA.

Transformation is the process by which cells have incorporated an exogenous gene by direct infection, transfection or other means of uptake.

The term "vector" is well understood and is synonymous with the often-used phrase "cloning vehicle". A vector is non-chromosomal double-stranded DNA comprising an intact replicon such that the vector is replicated when placed within a unicellular organism, for example by a process of transformation. Viral vectors include retroviruses, adenoviruses, herpesvirus, papovirus, or otherwise modified naturally occurring viruses. Vector also means a formulation of DNA with a chemical or substance which allows uptake by cells.

In another embodiment the present invention provides for inhibiting the expression of a gene. Four approaches may be utilized to accomplish this goal. These include the use of antisense agents, either synthetic oligonucleotides which are complementary to the mRNA (Maher III, L. J. and Dolnick, B. J. *Arch. Biochem. Biophys.,* 253, 214–220 (1987) and (Zamecnik, P. C., et al., *Proc. Natl. Acad. Sci.,* 83, 4143–4146 (1986)), or the use of plasmids expressing the reverse complement of this gene (Izant, J. H. and Weintraub, H., *Science,* 229, 345–352, (1985); *Cell,* 36, 1077–1015 (1984)). In addition, catalytic RNAs, called ribozymes, can specifically degrade RNA sequences (Uhlenbeck, O. C., *Nature,* 328, 596–600 (1987), Haseloff, J. and Gerlach, W. L., *Nature,* 334, 585–591 (1988)). The third approach involves "intracellular immunization", where analogues of intracellular proteins can interfere specifically with their function (Friedman, A. D., Triezenberg, S. J. and McKnight, S. L., *Nature,* 335, 452–454 (1988)), described in detail below.

The first approaches may be used to specifically eliminate transcripts in cells. The loss of transcript may be confirmed by S1 nuclease analysis, and expression of binding protein determined using a functional assay. Single-stranded oligonucleotide analogues may be used to interfere with the processing or translation of the transcription factor mRNA. Briefly, synthetic oligonucleotides or thiol-derivative analogues (20–50 nucleotides) complementary to the coding strand of the target gene may be prepared. These antisense agents may be prepared against different regions of the mRNA. They are complementary to the 5' untranslated region, the translational initiation site and subsequent 20–50 base pairs, the central coding region, or the 3' untranslated region of the gene. The antisense agents may be incubated with cells transfected prior to activation. The efficacy of antisense competitors directed at different portions of the messenger RNA may be compared to determine whether specific regions may be more effective in preventing the expression of these genes.

RNA can also function in an autocatalytic fashion to cause autolysis or to specifically degrade complementary RNA sequences (Uhlenbeck, O. C., *Nature,* 328, 596–600 (1987), Haseloff, J. and Gerlach, W. L., *Nature,* 334, 585–591 (1988), and Hutchins, C. J., et al, *Nucleic Acids Res.,* 14, 3627–3640 (1986)). The requirements for a successful RNA cleavage include a hammerhead structure with conserved RNA sequence at the region flanking this structure. Regions adjacent to this catalytic domain are made complementary to a specific RNA, thus targeting the ribozyme to specific cellular mRNAs. To inhibit the production of a specific target gene, the mRNA encoding this gene may be specifically degraded using ribozymes. Briefly, any GUG sequence within the RNA transcript can serve as a target for degradation by the ribozyme. These may be identified by DNA sequence analysis and GUG sites spanning the RNA transcript may be used for specific degradation. Sites in the 5' untranslated region, in the coding region, and in the 3' untranslated region may be targeted to determine whether one region is more efficient in degrading this transcript. Synthetic oligonucleotides encoding 20 base pairs of complementary sequence upstream of the GUG site, the hammerhead structure and ~20 base pairs of complementary sequence downstream of this site may be inserted at the relevant site in the cDNA. In this way, the ribozyme may be targeted to the same cellular compartment as the endogenous message. The ribozymes inserted downstream of specific enhancers, which give high level expression in specific cells may also be generated. These plasmids may be introduced into relevant target cells using electroporation and cotransfection with a neomycin resistant plasmid, pSV2-Neo or another selectable marker. The expression of these transcripts may be confirmed by Northern blot and S1 nuclease analysis. When confirmed, the expression of mRNA may be evaluated by S1 nuclease protection to determine whether expression of these transcripts reduces steady state levels of the target mRNA and the genes which it regulates. The level of protein may also be examined.

Genes may also be inhibited by preparing mutant transcripts lacking domains required for activation. Briefly, after the domain has been identified, a mutant form which is incapable of stimulating function is synthesized. This truncated gene product may be inserted downstream of the SV-40 enhancer in a plasmid containing the neomycin resistance gene (Mulligan, R. and Berg, P., *Science*, 209, 1422–1427 (1980) (in a separate transcription unit). This plasmid may be introduced into cells and selected using G418. The presence of the mutant form of this gene will be confirmed by S1 nuclease analysis and by immunoprecipitation. The function of the endogenous protein in these cells may be evaluated in two ways. First, the expression of the normal gene may be examined. Second, the known function of these proteins may be evaluated. In the event that this mutant intercellular interfering form is toxic to its host cell, it may be introduced on an inducible control element, such as metallothionein promoter. After the isolation of stable lines, cells may be incubated with Zn or Cd to express this gene. Its effect on host cells can then be evaluated.

Another approach to the inactivation of specific genes is to overexpress recombinant proteins which antagonize the expression or function of other activities. For example, if one wished to decrease expression of TPA (e.g., in a clinical setting of disseminate thrombolysis), one could overexpress plasminogen activator inhibitor.

Advances in biochemistry and molecular biology in recent years have led to the construction of "recombinant" vectors in which, for example, retroviruses and plasmids are made to contain exogenous RNA or DNA, respectively. In particular instances the recombinant vector can include heterologous RNA or DNA, by which is meant RNA or DNA that codes for a polypeptide ordinarily not produced by the organism susceptible to transformation by the recombinant vector. The production of recombinant RNA and DNA vectors is well understood and need not be described in detail. However, a brief description of this process is included here for reference.

For example, a retrovirus or a plasmid vector can be cleaved to provide linear RNA or DNA having ligatable termini. These termini are bound to exogenous RNA or DNA having complementary like ligatable termini to provide a biologically functional recombinant RNA or DNA molecule having an intact replicon and a desired phenotypical property.

A variety of techniques are available for RNA and DNA recombination in which adjoining ends of separate RNA or DNA fragments are tailored to facilitate ligation.

The exogenous, i.e., donor, RNA or DNA used in the present invention is obtained from suitable cells. The vector is constructed using known techniques to obtain a transformed cell capable of in vivo expression of the therapeutic agent protein. The transformed cell is obtained by contacting a target cell with a RNA or DNA-containing formulation permitting transfer and uptake of the RNA or DNA into the target cell. Such formulations include, for example, retroviruses, plasmids, liposomal formulations, or plasmids complexes with polycationic substances such as poly-L-lysine, DEAC-dextran and targeting ligands.

The present invention thus provides for the genetic alteration of cells as a method to transmit therapeutic or diagnostic agents to localized regions of the blood vessel for local or systemic purposes. The range of recombinant proteins which may be expressed in these cells is broad and varied. It includes gene transfer using vectors expressing such proteins as tPA for the treatment of thrombosis and restenosis, angiogenesis or growth factors for the purpose of revascularization, and vasoactive factors to alleviate vasoconstriction or vasospasm. This technique can also be extended to genetic treatment of inherited disorders, or acquired diseases, localized or systemic. The present invention may also be used to introduce normal cells to specific sites of cell loss, for example, to replace endothelium damaged during angioplasty or catheterization.

For example, in the treatment of ischemic diseases (thrombotic diseases), genetic material coding for tPA or modifications thereof, urokinase or streptokinase is used to transform the cells. In the treatment of ischemic organ (e.g., heart, kidney, bowel, liver, etc.) failure, genetic material coding for recollateralization agents, such as transforming growth factor $\alpha$ (TGF-$\alpha$), transforming growth factor $\beta$ (TGF-$\beta$), angiogenin, tumor necrosis factor $\alpha$, tumor necrosis factor $\beta$, acidic fibroblast growth factor or basic fibroblast growth factor can be used. In the treatment of vasomotor diseases, genetic material coding for vasodilators or vasoconstrictors may be used. These include atrial natriuretic factor, platelet-derived growth factor or endothelin. In the treatment of diabetes, genetic material coding for insulin may be used.

The present invention can also be used in the treatment of malignancies by placing the transformed cells in proximity to the malignancy. In this application, genetic material coding for diphtheria toxin, pertussis toxin, or cholera toxin may be used.

In one of its embodiments, the present invention provides for the therapy of malignancy by either stimulating an immune response against tumor cells or inhibiting tumor cell growth or metastasis by genetic modification in vivo. This approach differs from previous methods in which tumor cells are propagated, modified, and selected in vitro.

In accordance with this embodiment, the present method is used to deliver a DNA sequence or an RNA sequence, including recombinant genes, to tumor cells in vivo with (1) retroviral or viral vectors as vehicles, (2) DNA or RNA/liposome complexes as vehicles, (3) chemical formulations containing the DNA or RNA sequence and coupled to a carrier molecule which facilitates delivery of the sequence to the targeted cells, or (4) by utilizing cell-mediated gene transfer to deliver genes to specific sites in vivo, e.g., by relying upon the use of vascular smooth muscle cells or endothelia cells which have been transduced in vitro as a vehicle to deliver the recombinant gene into the site of the tumor.

In an aspect of this embodiment, the present invention relies on the immune system to provide protection against cancer and play an important role as an adjuvant treatment for a malignancy. Immunotherapy has shown promise as an adjuvant approach to the treatment of malignancies. Both cytolytic T cells and lymphokines can facilitate tumor cell destruction, and strategies to enhance tumor regression by administration of cytokines or tumor infiltrating lymphocytes have shown efficacy in animal models and human trials. For example, it is known that lymphokine activated killer cells (LAK) and tumor infiltrating lymphocytes (TIL) can lyse neoplastic cells and produce partial or complete tumor rejection. Expression of cytokine genes in malignant cells has also enhanced tumor regression.

The present invention provides a novel gene transfer approach against tumors by the introduction of recombinant genes directly into tumor cells in vivo, where, by contrast, traditional gene transfer techniques have focused on modification of tumor cells in vitro followed by transfer of the modified cells. The prior art approaches are disadvantageous because they subject the cells to selection in different growth conditions from those which act in vivo, and because they also require that cell lines be established for each malignancy, thereby rendering adaptability to human disease considerably more difficult.

Genes which may be used with this embodiment include genes containing a DNA sequence (or the corresponding RNA sequence may be used) encoding an intracellular, secreted, or cell surface molecule which is exogenous to the patient and which (1) is immunogenic to the patient, (2) induces rejection, regression, or both, of the tumor, or (3) is toxic to the cells of the tumor.

The vectors containing the DNA sequence (or the corresponding RNA sequence) which may be used in accordance with the invention may be an eukaryotic expression vector containing the DNA or the RNA sequence of interest. Techniques for obtaining expression of exogenous DNA or RNA sequences in a host are known. See, for example, Korman et al, *Proc. Nat. Acad. Sci.* (*USA*) (1987) 84:2150–2154, which is hereby incorporated by reference.

This vector, as noted above, may be administered to the patient in a retroviral or other viral vector (i.e., a viral vector) vehicle, a DNA or RNA/liposome complex, or by utilizing cell-mediated gene transfer. Further, the vector, when present in non-viral form, may be administered as a DNA or RNA sequence-containing chemical formulation coupled to a carrier molecule which facilitates delivery to the host cell. Such carrier molecule would include an antibody specific to the cells to which the vector is being delivered or a molecule capable of interacting with a receptor associated with the target cells.

Cell-mediated gene transfer may be used in accordance with the invention. In this mode, one relies upon the delivery of recombinant genes into living organisms by transfer of the genetic material into cells derived from the host and modification in cell culture, followed by the introduction of genetically altered cells into the host. An illustrative packaging cell line which may be used in accordance with this embodiment is described in Danos et al, *Proc. Natl. Acad. Sci.* (*USA*) (1988) 85:6460, which is hereby incorporated by reference.

The DNA or RNA sequence encoding the molecule used in accordance with the invention may be administered to the patient, which may be human or a non-human animal, either locally or systemically. The systemic administration is preferably carried out using the non-viral DNA or RNA chemical formulation coupled to a carrier molecule which facilitates delivery to the host cells. Any of the administrations may be performed by IV or IM injection or subcutaneous injection using any known means, or by the use of the catheter in accordance with the present invention.

The retroviral vector vehicles used in accordance with the present invention comprise a viral particle derived from a naturally-occurring retrovirus which has been genetically altered to render it replication defective and to express a recombinant gene of interest in accordance with the invention. Once the virus delivers its genetic material to a cell, it does not generate additional infectious virus but does introduce exogenous recombinant genes to the cell.

In other viral vectors, the virus particle used is derived from other naturally-occurring viruses which have been genetically altered to render them replication defective and to express recombinant genes. Such viral vectors may be derived from adenovirus, papillomavirus, herpesvirus, parvovirus, etc.

The sequences of the present invention may also be administered as DNA or RNA/liposome complex. Such complexes comprise a mixture of fat particles, lipids, which bind to genetic material, DNA or RNA, providing a hydrophobic coat, allowing genetic material to be delivered into cells. This formulation provides a non-viral vector for gene transfer. Liposomes used in accordance with the invention may comprise DOPE (dioleyl phosphatidyl ethanol amine), CUDMEDA (N-(5-cholestrum-3-β-ol 3-urethanyl)-N', N'-dimethlethylene diamine).

As noted above, other non-viral vectors may also be used in accordance with the present invention. These include chemical formulations of DNA or RNA coupled to a carrier molecule (e.g., an antibody or a receptor ligand) which facilitates delivery to host cells for the purpose of altering the biologic properties of the host cells. The term "chemical formulations" used herein refers to modifications of nucleic acids to allow coupling of the nucleic acid compounds to a protein or lipid, or derivative thereof, carrier molecule. Such carrier molecules include antibodies specific to the host cells or receptor ligands, i.e., molecules able to interact with receptors associated with the host cells.

The molecules which may be used in accordance with this invention, include the following: (1) genes encoding immune stimulants, such as Class I histocompatibility genes, Class II histocompatibility genes, bacterial genes, including mycobacterial (PPD) genes and genes encoding heat shock proteins, viral glycoproteins encoding genes, including vesicular stomatitis virus G protein, influenza hemagglutinin, and herpes virus glycoprotein β, minor histocompatibility antigens, foreign proteins, such as lysozyme or bovine serum albumin, and oncogenes, including EIA, P53 (mutants) and tax; (2) immune and growth stimulants/inhibitors, including inducers of differentiation, such as stimulants, including interleukin-2 (IL-2) IL-4, 3, 6 or 8, inhibitors/inducers of differentiation, such as TNF-α or β, TGF-β (1, 2 or 3), IL-1, soluble growth factor receptors (PDGF, FGF receptors), recombinant antibodies to growth factors or receptors, analogs of growth factors (PDGF, FGF), interferons (α, β or γ) and adhesion molecules; or (3) toxins or negative selectable markers, including thymidine kinase, diphtheria toxin, pertussis toxin or drug-sensitive proteins.

The DNA/RNA sequence is preferably obtained from a source of the same species as the patient, but this is not absolutely required, and the present invention provides for the use of DNA sequences obtained from a source of a species different from the patient in accordance with this embodiment. A preferred embodiment of the present invention, genes encoding immune stimulants and toxins or negative selectable markers, corresponding to (1) and (3) above, are preferably selected from a species different than the species to which the patient belongs. For immune and growth stimulants/inhibitors, corresponding to (2) above, in accordance with another preferred embodiment of the invention, one preferably employs a gene obtained from a species which is the same as the species of the patient.

In the use of the present invention in the treatment of AIDS, genetic material coding for soluble CD4 or derivatives thereof may be used. In the treatment of genetic diseases, for example, growth hormone deficiency, genetic material coding for the needed substance, for example, human growth hormone, is used. All of these genetic materials are readily available to one skilled in this art.

In another embodiment, the present invention provides a kit for treating a disease in a patient which contains a catheter and a solution which contains either an enzyme or a mild detergent, in which the catheter is adapted for insertion into a blood vessel and contains a main catheter body having a balloon element adapted to be inserted into said vessel and expansible against the walls of the blood vessel so as to hold the main catheter body in place in the blood vessel, and means carried by the main catheter body for delivering a solution into the blood vessel, and the solution which contains the enzyme or mild detergent is a physiologically acceptable solution. The solution may contain a proteolytic enzyme, such as dispase, trypsin, collagenase, papain, pepsin, or chymotrypsin. In addition to proteolytic enzymes, lipases may be used. As a mild detergent, the solution may contain NP-40, Triton X100, deoxycholate, SDS or the like.

Alternatively, the kit may contain a physiological acceptable solution which contains an agent such as heparin, poly-L-lysine, polybrene, dextran sulfate, a polycationic material, or bivalent antibodies. This solution may also contain vectors or cells (normal or transformed). In yet another embodiment the kit may contain a catheter and both a solution which contains an enzyme or mild detergent and a solution which contains an agent such as heparin, poly-L-lysine, polybrene, dextran sulfate, a polycationic material or bivalent antibody and which may optionally contain vectors or cells.

The kit may contain a catheter with a single balloon and central distal perfusion port, together with acceptable solutions to allow introduction of cells in a specific organ or vectors into a capillary bed or cells in a specific organ or tissue perfused by this capillary bed.

Alternatively, the kit may contain a main catheter body which has two spaced balloon elements adapted to be inserted in a blood vessel with both being expansible against the walls of the blood vessel for providing a chamber in the blood vessel, and to hold the main catheter body in place. In this case, the means for delivering a solution into the chamber is situated in between the balloon elements. The kit may contain a catheter which possesses a plurality of port means for delivering the solution into the blood vessel.

Thus, the present invention represents a method for treating a disease in a patient by causing a cell attached onto the walls of a vessel or the cells of an organ perfused by this vessel in the patient to express an exogeneous therapeutic agent protein, wherein the protein treats the disease or may be useful for diagnostic purposes. The present method may be used to treat diseases, such as an ischemic disease, a vasomotor disease, diabetes, a malignancy, AIDS or a genetic disease.

The present method may use exogeneous therapeutic agent proteins, such as tPA and modifications thereof, urokinase, streptokinase, acidic fibroblast growth factor, basic fibroblast growth factor, tumor necrosis factor α, tumor necrosis factor β, transforming growth factor α, transforming growth factor β, atrial natriuretic factor, platelet-derived growth factor, endothelian, insulin, diphtheria toxin, pertussis toxin, cholera toxin, soluble CD4 and derivatives thereof, and growth hormone to treat diseases.

The present method may also use exogenous proteins of diagnostic value. For example, a marker protein, such as β-galatosodase, may be used to monitor cell migration.

It is preferred, that the cells caused to express the exogenous therapeutic agent protein be endothelial cells.

Other features of the present invention will become apparent in the course of the following descriptions of exemplary embodiments which are given for illustration of the invention and are not intended to be limiting thereof.

The data reported below demonstrate the feasibility of endothelial cell transfer and gene transplantation; that endothelial cells may be stably implanted in situ on the arterial wall by catheterization and express a recombinant marker protein, β-galactosidase, in vivo.

Because atherogenesis in swine has similarities to humans, an inbred pig strain, the Yucatan minipig (Charles River Laboratories, Inc., Wilmington, Mass.), was chosen as an animal model (1). A primary endothelial cell line was established from the internal jugular vein of an 8 month-old female minipig. The endothelial cell identity of this line was confirmed in that the cells exhibited growth characteristics and morphology typical of porcine endothelium in tissue culture. Endothelial cells also express receptors for the acetylated form of low density lipoprotein (AcLDL), in contrast to fibroblasts and other mesenchymal cells (2). When analyzed for AcLDL receptor expression, greater than 99% of the cultured cells contained this receptor, as judged by fluorescent AcLDL uptake.

Two independent β-galactosidase-expressing endothelial lines were isolated following infection with a murine amphotropic β-galactosidase-transducing retroviral vector (BAG), which is replication-defective and contains both β-galactosidase and neomycin resistance genes (3). Cells containing this vector were selected for their ability to grow in the presence of G-418. Greater than 90% of selected cells synthesized β-galactosidase by histochemical staining. The endothelial nature of these genetically altered cells was also confirmed by analysis of fluorescent AcLDL uptake. Infection by BAG retrovirus was further verified by Southern blot analysis which revealed the presence of intact proviral DNA at approximately one copy per genome.

Endothelial cells derived from this inbred strain, being syngeneic, were applicable for study in more than one minipig, and were tested in nine different experimental subjects. Under general anesthesia, the femoral and iliac arteries were exposed, and a catheter was introduced into the vessel (FIG. 1). Intimal tissues of the arterial wall were denuded mechanically by forceful passage of a partially inflated balloon catheter within the vessel. The artery was rinsed with heparinized saline and incubated with the neutral protease, dispase (50 U/ml), which removed any remaining luminal endothelial cells. Residual enzyme was rapidly inactivated by a2 globulin in plasma upon deflating the catheter balloons and allowing blood to flow through the vessel segment. The cultured endothelial cells which expressed β-galactosidase were introduced using a specially designed arterial catheter (USCI, Billerica, Mass.) that contained two balloons and a central instillation port (FIG. 1). When these balloons were inflated, a protected space was created within the artery into which cells were instilled through the central port 3 (FIG. 1). These endothelial cells, which expressed β-galactosidase, were allowed to incubate for 30 minutes to facilitate their attachment to the denuded vessel. The catheter was then removed, the arterial branch ligated, and the incision closed.

Segments of the artery innoculated with β-galactosidase-expressing endothelium were removed 2 to 4 weeks later. Gross examination of the arterial specimen after staining using the X-gal chromagen showed multiple areas of blue coloration, compared to an artery seeded with uninfected endothelium, indicative of β-galactosidase activity. Light microscopy documented β-galactosidase staining primarily in endothelial cells of the intima in experimentally seeded vessels.

In contrast, no evidence of similar staining was observed in control segments which had received endothelial cells containing no β-galactosidase. β-Galactosidase staining was occasionally evident in deeper intimal tissues, suggesting entrapment or migration of seeded endothelium within the previously injured vessel wall. Local thrombosis was observed in the first two experimental subjects. This complication was minimized in subsequent studies by administering acetylsalicylic acid prior to the endothelial cell transfer procedure and use of heparin anticoagulation at the time of innoculation. In instances of thrombus formation, β-galactosidase staining was seen in endothelial cells extending from the vessel wall to the surface of the thrombus.

A major concern of gene transplantation in vivo relates to the production of replication-competent retrovirus from genetically engineered cells. In these tests, this potential problem has been minimized through the use of a replication defective retrovirus. No helper virus was detectable among these lines after 20 passages in vitro. Although defective viruses were used because of their high rate of infectivity and their stable integration into the host cell genome (4), this approach to gene transfer is adaptable to other viral vectors.

A second concern involves the longevity of expression of recombinant genes in vivo. Endothelial cell expression of β-galactosidase appeared constant in vessels examined up to six weeks after introduction into the blood vessel in the present study.

These tests have demonstrated that genetically-altered endothelial cells can be introduced into the vascular wall of the Yucatan minipig by arterial catheterization. Thus, the present method can be used for the localized biochemical treatment of vascular disease using genetically-altered endothelium as a vector.

A major complication of current interventions for vascular disease, such as balloon angioplasty or insertion of a graft into a diseased vessel, is disruption of the atherosclerotic plaque and thrombus formation at sites of local tissue trauma (5). In part, this is mediated by endothelial cell injury (6). The present data show that genetically-altered endothelial cells can be introduced at the time of intervention to minimize local thrombosis.

This technique can also be used in other ischemic settings, including unstable angina or myocardial infarction. For instance, antithrombotic effects can be achieved by introducing cells expressing genes for tissue plasminogen activator or urokinase. This technology is also useful for the treatment of chronic tissue ischemia. For example, elaboration of angiogenic or growth factors (7) to stimulate the formation of collateral vessels to severely ischemic tissue, such as the myocardium. Finally, somatic gene replacement for systemic inherited diseases is feasible using modifications of this endothelial cell gene transfer technique.

Experimental section:

A. Analysis of AcLDL receptor expression in normal and β-galactosidase-transduced porcine endothelial cells.

Endothelial cell cultures derived from the Yucatan minipig, two sublines infected with BAG retrovirus or 3T3 fibroblast controls were analyzed for expression of AcLDL receptor using fluorescent labelled AcLDL.

Endothelial cells were derived from external jugular veins using the neutral protease dispase (8). Excised vein segments were filled with dispase (50 U/ml in Hanks' balanced salt solution) and incubated at 30° C. for 20 minutes. Endothelium obtained by this means was maintained in medium 199 (GIBCO, Grand Island, N.Y.) supplemented with fetal calf serum (10%), 50 μg/ml endothelial cell growth supplement (ECGS) and heparin (100 μg/ml). These cells were infected with BAG retrovirus, and selected for resistance to G-418. Cell cultures were incubated with (1,1'-dioctadecyl-3,3,3',3'-tetramethylindocarbacyanine perchlorate) (Dil) AcLDL (Biomedical Technologies, Stoughton, Mass.) (10 μg/ml) for 4–6 hrs. at 37° C., followed by three rinses with phosphate-buffered saline containing 0.5% glutaraldehyde. Cells were visualized by phase contrast and fluorescent microscopy.

B. Method of introduction of endothelial cells by catheterization.

A double balloon catheter was used for instillation of endothelial cells. The catheter has a proximal and distal balloon, each 6 mm in length and 5 mm in width, with a 20 mm length between the balloons. The central section of the catheter has a 2 mm pore connected to an instillation port. Proximal and distal balloon inflation isolates a central space, allowing for instillation of infected cells through the port into a discrete segment of the vessel. For a schematic representation of cell introduction by catheter, see FIGS. 1 and 2.

Animal care was carried out in accordance with "Principles of Laboratory Animal Care" and "Guide for the Care and Use of Laboratory Animals" (NIH publication No. 80-23, Revised 1978). Female Yucatan minipigs (80–100 kg) were anesthetized with pentobarbital (20 mg/kg), intubated, and mechanically ventilated. These subjects underwent sterile surgical exposure of the iliac and femoral arteries. The distal femoral artery was punctured, and the double-balloon catheter was advanced by guidewire into the iliac artery. The external iliac artery was identified; the proximal balloon was partially inflated and passed proximally and distally so as to mechanically denude the endothelium. The catheter was then positioned with the central space located in the region of denuded endothelium, and both balloons were inflated. The denuded segment was irrigated with heparinized saline, and residual adherent cells were removed by instillation of dispase (20 U/ml) for 10 min. The denuded vessel was further irrigated with a heparin solution and the BAG-infected endothelial cells were instilled for 30 min. The balloon catheter was subsequently removed, and antegrade blood flow was restored. The vessel segments were excised 2 to 4 weeks later. A portion of the artery was placed in 0.5% glutaraldehyde for five minutes and stored in phosphate-buffered saline, and another portion was mounted in a paraffin block for sectioning. The presence of retroviral expressed β-galactosidase was determined by a standard histochemical technique (19).

C. Analysis of endothelial cells in vitro and in vivo.

β-Galactosidase activity was documented by histochemical staining in (A) primary endothelial cells from the Yucatan minipig, (B) a subline derived by infection with the BAG retroviral vector, (C) a segment of normal control artery, (D) a segment of artery instilled with endothelium infected with the BAG retroviral vector, (E) microscopic cross-section of normal control artery, and (F) microscopic cross-section of artery instilled with endothelium infected with the BAG retroviral vector.

Endothelial cells in tissue culture were fixed in 0.5% glutaraldehyde prior to histochemical staining. The enzymatic activity of the *E. coli* β-galactosidase protein was used to identify infected endothelial cells in vitro and in vivo. The β-galactosidase transducing Mo-MuLV vector (2), (BAG)

was kindly provided by Dr. Constance Cepko. This vector used the wild type Mo-MuLV LTR as a promoter for the β-galactosidase gene. The simian virus 40 (SV-40) early promoter linked to the Tn5 neomycin resistance gene provides resistance to the drug G-418 and is inserted downstream of the β-galactosidase gene, providing a marker to select for retrovirus-containing, β-galactosidase expressing cells. This defective retrovirus was prepared from fibroblast ψ am cells (3,10), and maintained in Dulbecco's modified Eagle's medium (DMEM) and 10% calf serum. Cells were passaged twice weekly following trypsinization. The supernatant, with titers of $10^4$–$10^5$/ml G-418 resistant colonies, was added to endothelial cells at two-thirds confluence and incubated for 12 hours in DMEM with 10% calf serum at 37° C. in 5% $CO_2$ in the presence of 8 µg/ml of polybrene. Viral supernatants were removed, and cells maintained in medium 199 with 10% fetal calf serum, ECGS (50 µg/ml), and endothelial cell conditioned medium (20%) for an additional 24 to 48 hours prior to selection in G-418 (0.7 µg/ml of a 50% racemic mixture). G-418 resistant cells were isolated and analyzed for β-galactosidase expression using a standard histochemical stain (9). Cells stably expressing the β-galactosidase enzyme were maintained in continuous culture for use as needed. Frozen aliquots were stored in liquid nitrogen.

PUBLICATIONS CITED

1. J. S Reitman, R. W. Mahley, D. L. Fry, *Atherosclerosis* 43, 119 (1982).
2. R. E. Pitos, T. L. Innerarity, J. N. Weinstein, R. W. Mahley, *Arteriosclerosis* 1, 177 (1981); T. J. C. Van Berkel, J. F. Kruijt *FEBS Lett.* 132, 61 (1981); J. C. Voyta, P. A. Netland, D. P. Via, E. P. Zetter, *J. Cell. Biol.*, 99, 81A (abstr.) (1984); J. M. Wilson, D. E. Johnston, D. M. Jefferson, R. C. Mulligan, *Proc. Natl. Acad. Sci. U.S.A.*, 84, 4421 (1988).
3. J. Price, D. Turner, C. Cepko, *Proc. Natl. Acad. Sci. U.S.A.*, 84, 156 (1987).
4. R. Mann, R. C. Mulligan, D. Baltimore, *Cell* 33, 153 (1983); C. L. Cepko, B. E. Roberts, R. C. Mulligan, *Cell* 37, 1053 (1984); M. A. Eglitis, W. F. Anderson, *Biotechniques* 6, 608 (1988).
5. S. G. Ellis, G. S. Roubin, S. B. King, J. S. Douglas, W. S. Weintraub et al., *Circulation* 77, 372 (1988); L. Schwartz, M. G. Bourassa, J. Lesperance, H. E. Aldrige, F. Kazim, et al., *N. Engl. J. Med.* 318, 1714 (1988).
6. P. C. Block, R. K. Myler, S. Stertzer, J. T. Fallon, *N. Engl. J. Med.* 305, 382 (1981); P. M. Steele, J. H. Chesebro, A. W. Stanson, *Circ. Res.* 57, 105 (1985); J. R. Wilentz, T. A. Sanborn, C. C. Handenschild, C. R. Valeri, T. J. Ryan, D. P. Faxon, *Circulation* 75, 636 (1987); W. McBride, R. A. Lange, L. D. Hillis, N. Engl. *J. Med.* 318, 1734 (1988).
7. J. Folkman, M. Klagsbrun, *Science* 235, 442 (1987); S. J. Leibovich, P. J. Polverini, H. Michael Shepard, D. M. Wiseman, V. Shively, N. Nuseir, *Nature* 329, 630 (1987); J. Folkman, M. Klagsbrun, *Nature* 329, 671 (1987).
8. T. Matsumura, T. Yamanka, S. Hashizume, Y. Irie, K. Nitta, Japan. *J. Exp. Med.* 45, 377 (1975); D. G. S. Thilo, S. Muller-Kusel, D. Heinrich, I. Kauffer, E. Weiss, *Artery*, 8, 25a (1980).
9. A. M. Dannenberg, M. Suga, in *Methods for Studying Mononuclear Phagocytes*, D. O. Adams, P. J. Edelson, H. S. Koren, Eds. (Academic Press, New York, 1981), pp 375–395.
10. R. D. Cone, R. C. Mulligan, *Proc. Natl. Acad. Sci. U.S.A.* 81, 6349 (1984).

Obviously, numerous modifications and variations of the present invention are possible in light of the above teachings. It is therefore to be understood that within the scope of the appended claims, the invention may be practiced otherwise than as specifically described herein.

What is new and desired to be secured by Letters Patent of the United States is:

1. A method of transforming cells surrounding a solid tumor in a mammal, which comprises directly injecting into said solid tumor a viral vector containing a nucleic acid sequence encoding a protein selected from the group consisting of a Class I histocompatibility protein, a Class II histocompatibility protein, a cytokine, diphtheria toxin, and pertussis toxin in an amount effective for transforming said cells, wherein said protein is expressed by said cells.

2. A method of in vivo site-specifically transforming cells in a solid tumor in a mammal, or in tissues surrounding said solid tumor, which comprises introducing into said mammal by direct injection at said solid tumor a viral vector containing a nucleic acid sequence encoding a protein selected from the group consisting of a Class I histocompatibility protein, a Class II histocompatibility protein, a cytokine, diphtheria toxin, and pertussis toxin in an amount effective for transforming said cells or tissues, such that cells or tissues express said protein.

3. The method of claim 2, wherein said protein is immunogenic to said patient.

4. The method of claim 2, wherein said protein induces cellular differentiation.

5. The method of claim 2, wherein said nucleic acid sequence is obtained from a species which is the same as said mammal.

6. The method of claim 2, wherein said nucleic acid sequence is obtained from a species different than the species of said mammal.

7. The method of claim 2, wherein said nucleic acid sequence is administered as a nucleic acid/liposome complex.

8. The method of claim 2, wherein said protein is selected from the group consisting of a Class I histocompatibility protein and a Class II histocompatibility protein.

9. The method of claim 2, wherein said cytokine is selected from the group consisting of interleukin-1, interleukin-2, interleukin-3, interleukin-4, interleukin-6, interleukin-8, tumor necrosis factor-α, tumor necrosis factor-β1, tumor necrosis factor-β2, tumor necrosis factor-β3, interferon α, interferon β, and interferon γ.

10. The method of claim 2, wherein said protein is selected from the group consisting of diphtheria toxin, and pertussis toxin.

11. The method of claim 2, wherein said nucleic acid encodes a cytokine selected from the group consisting of interleukin-1, interleukin-2, interleukin-3, interleukin-4, interleukin-6, interleukin-8, tumor necrosis factor-α, tumor necrosis factor-β1, tumor necrosis factor-β2, tumor necrosis factor-β3, interferon α, and interferon β.

12. The method of claim 11, wherein said nucleic acid sequence encodes interleukin-2.

13. The method of claim 2, wherein said viral vector is an adenoviral vector.

14. A method of in vivo site-specifically transforming cells in a solid tumor in a mammal, or in tissues surrounding said solid tumor, which comprises introducing into said mammal by direct injection at said solid tumor a nucleic acid sequence encoding a protein selected from the group consisting of a Class I histocompatibility protein, a Class II histocompatibility protein, a cytokine, diphtheria toxin, and pertussis toxin in an amount effective for transforming said cells or tissues, such that cells or tissues express said protein.

15. The method of claim 14, wherein said protein is immunogenic to said patient.

16. The method of claim 14, wherein said protein induces cellular differentiation.

17. The method of claim 14, wherein said nucleic acid sequence is obtained from a species which is the same as said mammal.

18. The method of claim 14, wherein said nucleic acid sequence is obtained from a species different than the species of said mammal.

19. The method of claim 14, wherein said nucleic acid sequence is administered as a nucleic acid/liposome complex.

20. The method of claim 14, wherein said protein is selected from the group consisting of a Class I histocompatibility protein and a Class II histocompatibility protein.

21. The method of claim 14, wherein said cytokine is selected from the group consisting of interleukin-1, interleukin-2, interleukin-3, interleukin-4, interleukin-6, interleukin-8, tumor necrosis factor-α, tumor necrosis factor-β1, tumor necrosis factor-β2, tumor necrosis factor-β3, interferon α, interferon β, and interferon γ.

22. The method of claim 14, wherein said protein is selected from the group consisting diphtheria toxin, and pertussis toxin.

23. The method of claim 14, wherein said nucleic acid encodes a cytokine selected from the group consisting of interleukin-1, interleukin-2, interleukin-3, interleukin-4, interleukin-6, interleukin-8, tumor necrosis factor-α, tumor necrosis factor-β1, tumor necrosis factor-β2, tumor necrosis factor-β3, interferon α, and interferon β.

24. The method of claim 23, wherein said nucleic acid sequence encodes interleukin-2.

* * * * *